US006091842A

United States Patent [19]
Domanik et al.

[11] Patent Number: 6,091,842
[45] Date of Patent: *Jul. 18, 2000

[54] CYTOLOGICAL SPECIMEN ANALYSIS SYSTEM WITH SLIDE MAPPING AND GENERATION OF VIEWING PATH INFORMATION

[75] Inventors: Richard A. Domanik, Libertyville; Vladimir Dadeshidze, Buffalo Grove; Lars J. Olsson, Chicago, all of Ill.

[73] Assignee: AccuMed International, Inc., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/736,790
[22] Filed: Oct. 25, 1996
[51] Int. Cl.[7] .................................. G06K 9/00; G21K 7/00
[52] U.S. Cl. ............................ 382/133; 250/201.3; 348/79; 359/382; 378/43; 396/432; 427/2.11
[58] Field of Search .......................... 128/920, 922–924; 250/461.2, 201.3; 356/39; 377/10; 382/128–134, 100; 600/309; 348/79; 359/382; 378/43; 396/432; 427/2.11

[56] References Cited

U.S. PATENT DOCUMENTS

| | | | |
|---|---|---|---|
| 3,416,250 | 12/1968 | Schweers | 206/456 |
| 3,418,456 | 12/1968 | Hamisch et al. | 235/464 |
| 3,600,556 | 8/1971 | Acker | 235/61.11 |
| 3,745,314 | 7/1973 | Mathias et al. | 235/61.11 |
| 3,851,972 | 12/1974 | Smith et al. | 356/72 |
| 3,902,615 | 9/1975 | Levy et al. | 214/301 |
| 4,141,458 | 2/1979 | Brooks et al. | 214/301 |
| 4,142,863 | 3/1979 | Covington et al. | 422/63 |
| 4,175,860 | 11/1979 | Bacus | 356/39 |
| 4,250,405 | 2/1981 | Ashcroft et al. | 235/456 |
| 4,367,915 | 1/1983 | Georges | 350/530 |
| 4,402,613 | 9/1983 | Daly et al. | 356/446 |
| 4,404,683 | 9/1983 | Kobayashi et al. | 382/134 |
| 4,422,105 | 12/1983 | Rodesch et al. | 358/903 |

(List continued on next page.)

FOREIGN PATENT DOCUMENTS

| | | |
|---|---|---|
| 849379 | 8/1970 | Canada . |
| 1272285 | 7/1990 | Canada . |
| 1299179 | 4/1992 | Canada . |
| 1304612 | 7/1992 | Canada . |
| 2042075 | 11/1992 | Canada . |
| 2086785 | 4/1994 | Canada . |
| 2086786 | 4/1994 | Canada . |
| 453 239 A1 | 10/1991 | European Pat. Off. . |
| 577 084 A2 | 1/1994 | European Pat. Off. . |
| 0 647 844 A2 | 4/1995 | European Pat. Off. . |

(List continued on next page.)

OTHER PUBLICATIONS

Search report in GB–9619298.4 (Dec. 2, 1996).
Search report in GB–9619297.6 (Nov. 18, 1996).

(List continued on next page.)

*Primary Examiner*—Jon Chang
*Assistant Examiner*—Jayanti K. Patel
*Attorney, Agent, or Firm*—McDonnell Boehnen Hulbert & Berghoff

[57] ABSTRACT

A cytological specimen analyzer includes an image capture apparatus, a mapper and a screening station. The mapper receives digital images of regions of a slide containing a cytological specimen and determines if each of the regions contains cytological material. The mapper analyzes the image of each region, pixel by pixel, and if the region contains cytological material then the coordinates of the region are stored along with a focal position for the region and a value indicative of the amount of cytological material in the region. Upon analysis of each region on the slide, the mapper determines the most efficient path to be traveled between regions containing cytological material to minimize the viewing time of an operator at the screening station. Upon request by the screening station, the sequence of the aforesaid coordinates, which is indicative of the most efficient path, are transmitted to the screening station.

28 Claims, 7 Drawing Sheets

U.S. PATENT DOCUMENTS

| | | | |
|---|---|---|---|
| 4,427,332 | 1/1984 | Manriquez | 414/331 |
| 4,449,042 | 5/1984 | Hampson et al. | 235/464 |
| 4,513,438 | 4/1985 | Graham et al. | 382/134 |
| 4,588,341 | 5/1986 | Motoda | 414/32 |
| 4,628,193 | 12/1986 | Blum | 235/375 |
| 4,658,960 | 4/1987 | Iwasa | 206/459 |
| 4,812,909 | 3/1989 | Yokobayashi et al. | 348/589 |
| 4,858,014 | 8/1989 | Zeevi et al. | 358/217 |
| 4,965,725 | 10/1990 | Rutenberg | 364/413.1 |
| 5,021,218 | 6/1991 | Davis et al. | 422/104 |
| 5,068,906 | 11/1991 | Kosaka | 382/133 |
| 5,081,038 | 1/1992 | Sugaya et al. | 436/46 |
| 5,154,889 | 10/1992 | Muraishi | 422/65 |
| 5,209,903 | 5/1993 | Kanamori et al. | 422/65 |
| 5,245,530 | 9/1993 | Taki | 364/167.01 |
| 5,257,182 | 10/1993 | Luck et al. | 382/224 |
| 5,260,556 | 11/1993 | Lake et al. | 235/494 |
| 5,270,006 | 12/1993 | Uchigaki et al. | 422/63 |
| 5,287,182 | 2/1994 | Haskell et al. | 348/500 |
| 5,287,272 | 2/1994 | Rutenberg et al. | 364/413.01 |
| 5,332,549 | 7/1994 | MacIndoe, Jr. | 422/63 |
| 5,333,207 | 7/1994 | Rutenberg | 382/133 |
| 5,364,790 | 11/1994 | Atwood et al. | 435/288 |
| 5,380,488 | 1/1995 | Wakatake | 422/65 |
| 5,513,013 | 4/1996 | Kuo | 358/448 |
| 5,526,258 | 6/1996 | Bacus | 364/413.1 |
| 5,528,703 | 6/1996 | Lee | 382/257 |
| 5,544,650 | 8/1996 | Boon et al. | 600/309 |
| 5,548,661 | 8/1996 | Price et al. | 382/133 |
| 5,625,705 | 4/1997 | Recht | 382/133 |
| 5,627,908 | 5/1997 | Lee et al. | 382/133 |
| 5,655,029 | 8/1997 | Rutenberg et al. | 382/133 |
| 5,671,288 | 9/1997 | Wilhelm et al. | 382/128 |
| 5,677,966 | 10/1997 | Doerrer et al. | 382/128 |
| 5,710,842 | 1/1998 | Lee | 382/128 |
| 5,715,326 | 2/1998 | Ortyn et al. | 382/133 |
| 5,715,327 | 2/1998 | Wilhelm et al. | 382/134 |
| 5,740,269 | 4/1998 | Oh et al. | 382/133 |
| 5,745,601 | 4/1998 | Lee et al. | 382/133 |
| 5,757,954 | 5/1998 | Kuan et al. | 382/128 |

FOREIGN PATENT DOCUMENTS

| | | |
|---|---|---|
| 30 40 245 A1 | 8/1981 | Germany . |
| 33 13789 A1 | 10/1983 | Germany . |
| 195 48 091 A1 | 7/1996 | Germany . |
| 63-305510 | 12/1988 | Japan . |
| 1 439 986 | 6/1976 | United Kingdom . |
| 2 118 716 A | 11/1983 | United Kingdom . |
| 2 145 544 | 3/1985 | United Kingdom . |
| 2 212 301 | 7/1989 | United Kingdom . |
| 2 219 104 | 11/1989 | United Kingdom . |
| WO 87/01214 | 2/1987 | WIPO . |
| WO 90/07162 | 6/1990 | WIPO . |
| WO 91/06911 | 5/1991 | WIPO . |
| WO 91/15826 | 10/1991 | WIPO . |
| WO 92/13308 | 8/1992 | WIPO . |
| WO 93/16436 | 8/1993 | WIPO . |
| WO 95/02204 | 1/1995 | WIPO . |
| WO 95/22749 | 8/1995 | WIPO . |
| WO 96/03709 | 2/1996 | WIPO . |
| WO 97/25678 | 7/1997 | WIPO . |

OTHER PUBLICATIONS

Search report in GB–9619296.8 (Jan. 21, 1997).

"Autostage System," Photonics Spectra, p. 165, Jun. 1994.

"Nikon Biostation® creates a fully automated cytology workstation in your laboratory," Nikon Inc. Instrument Group, Melville, NY, Feb. 1994.

The LEP Robotic Slide Handling System by LUDL Electronic Products, Ltd.

Search Report in United Kingdom Patent Application No. GB 9722555.1, dated Jan. 14, 1998.

Search report in GB 9722555.1 (Jan. 14, 1998).

International Search Report in PCT/US98/14714, dated Oct. 27, 1998.

International Search Report in PCT/US98/14719, dated Oct. 27, 1998.

$$\begin{array}{ccccc} -1 & -1 & -1 & -1 & -1 \\ -1 & 1 & 1 & 1 & -1 \\ -1 & 1 & \mathbf{1} & 1 & -1 \\ -1 & 1 & 1 & 1 & -1 \\ -1 & -1 & -1 & -1 & -1 \end{array}$$

CYTOLOGICAL SPECIMEN ANALYSIS SYSTEM WITH SLIDE MAPPING AND GENERATION OF VIEWING PATH INFORMATION

FIELD OF THE INVENTION

This invention relates in general to the field of cytological specimen analysis and in particular to methods and apparatus employed in the visual screening of cytological specimens.

BACKGROUND OF THE INVENTION

Proper screening of cytological specimens is an important step in the diagnosis of numerous potentially serious maladies. For instance, in the case of Pap smears which are routinely taken for women, accurate screening of the Pap smear can detect the early stages of cancer, thus reducing the chances of any cancer or related abnormal condition from spreading. Typically such screening is performed by a highly trained technician, commonly referred to as a cytotechnologist.

To perform such a screening, the cytotechnologist generally views the slide containing the Pap smear through a microscope to detect the presence of cells which may exhibit cancerous or other abnormal conditions. While the analysis performed by the cytotechnologist requires intensive training, the process of thoroughly screening a specimen for the presence of cancerous or abnormal cells is often laborious and tedious. To ensure an accurate analysis the entire specimen must be viewed to determine the presence or absence of an abnormal condition. While many specimens may have portions containing no cytological material, the cytotechnologist must nevertheless view the entire specimen to determine this fact.

Automated microscopes which simplify or reduce the manual effort required of the cytotechnologist are often helpful in increasing the efficiency with which a specimen may be screened. Other automation techniques, such as generally described by B. Nordin in a doctoral thesis entitled "The Development of an Automatic Prescreener for the Early Detection of Cervical Cancer: Algorithms and Implementation", Uppsala University, Image Analysis Laboratory, Uppsala, Sweden (1989), are also helpful in increasing the cytological screening efficiency.

While such techniques may improve cytological screening efficiency by varying amounts, there exists a need for a system which reduces the time required to accurately analyze a cytological specimen and thereby increase the efficiency by which such a specimen may be analyzed.

SUMMARY OF THE INVENTION

It is a primary object of the present invention to reduce the average time required for the visual screening of cytological specimens. The foregoing object is achieved by providing a cytological specimen analyzer which presents to an operator only those fields of view that may contain diagnostically significant material. The cytological specimen analyzer includes a means which is responsive to an image of a portion of a cytological specimen, for determining if the portion contains viewable specimen material. A means which is responsive to the image containing viewable specimen material stores coordinates indicative of the location of the image on the cytological specimen. A means which is responsive to a plurality of the stored coordinates, each indicative of a location on the cytological specimen for a corresponding image, generates a routing path which minimizes the time required for a viewer of the cytological specimen to view each of the images which contain a viewable portion of a specimen.

Embodiments employing the foregoing principles advantageously reduce the amount of time required to view portions of the slide containing no cytological material in two ways. First, many regions of the slide containing no cytological material are identified and eliminated from the views presented to the viewer of the cytological specimen. Second, the path between the views to be presented is optimized, thus further reducing the amount of time required to view the cytological material on the slide. The efficiency of the analysis is thus increased and operator fatigue is decreased by increasing the proportion of time spent by the operator on analysis of actual cytological material.

In addition, embodiments utilizing the principles of the present invention present the cytotechnologist with the actual specimen on the slide for analysis rather than presenting an electronic image. The direct visual image seen through a microscope has better spatial resolution and color fidelity than an equivalent image which has been electronically captured and displayed, and therefore, the direct image is better suited for critical diagnostic applications. Moreover, the cytotechnologist is presented with all regions of the slide which contain cytological material, normal or abnormal, and thus uses his/her own skill and judgment in deciding whether the specimen contains abnormalities. Presentation of all of the cytological material contained in the specimen advantageously allows the cytotech to use contextual information in arriving at a determination, and use of the cytotech's training and skill allows detection of abnormalities which computerized image analysis systems may not be programmed to detect. Systems operating in accordance with the present invention can thus accommodate a wide range of sample types and preparations while computerized image analysis systems programmed to detect certain abnormalities can accommodate only those specific types and preparations of specimens for which they are programmed.

These and other features and advantages of the present invention may be better understood by considering the following detailed description of certain preferred embodiments of the invention. In the course of this description, reference will be made to the attached drawings.

DETAILED DESCRIPTION

Figure 1:
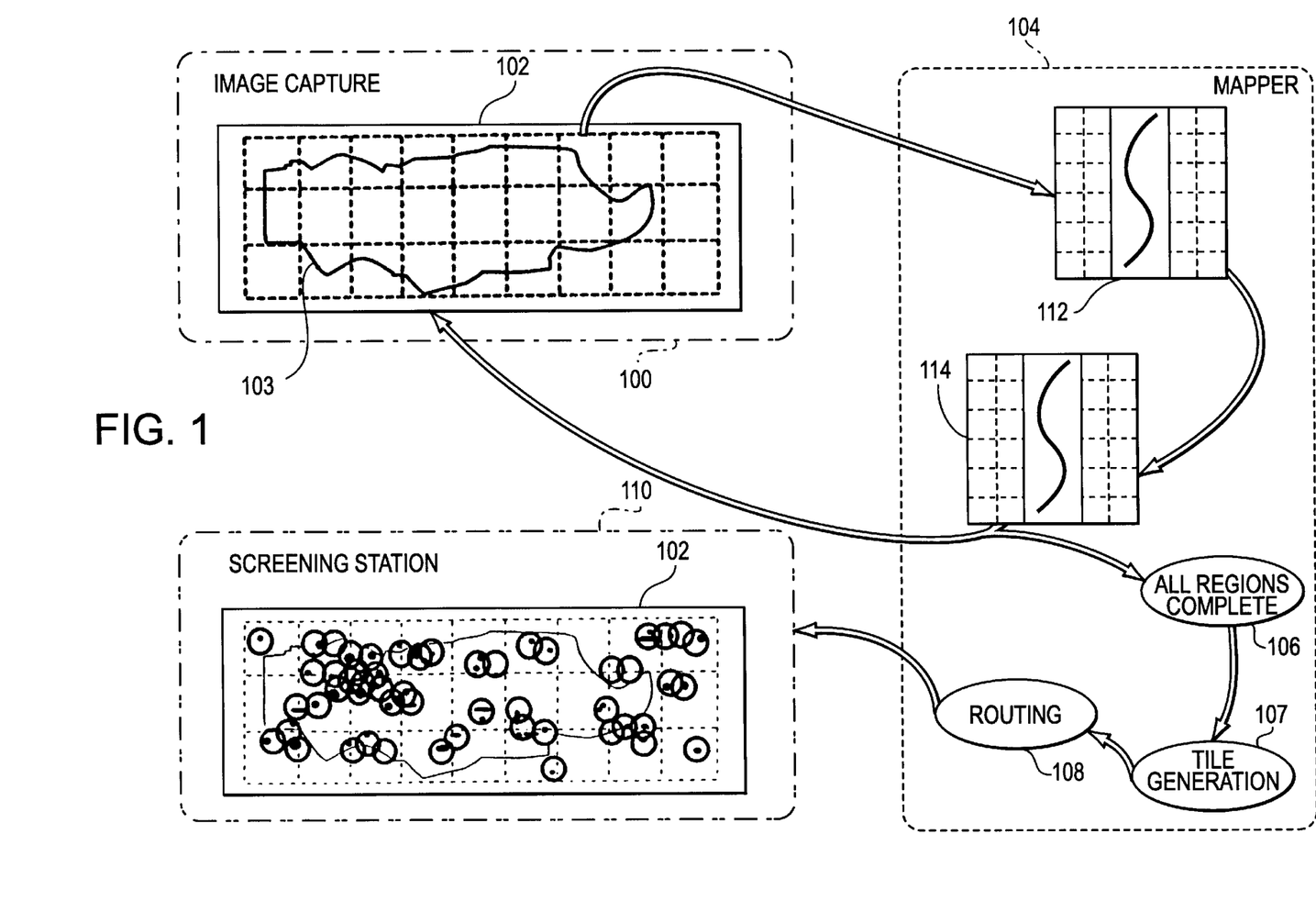
FIG. 1 is a flow diagram illustrating principal components employed and functions performed by a preferred embodiment.

FIG. 1 of the drawings shows by way of example, the functions performed by a cytological screening system employing the principles of the present invention. The cytological screening system of FIG. 1, which is adapted for use in a clinical laboratory or like facility, preferably includes image capture apparatus 100, a mapper 104 and a screening station 110 which includes a microscope for viewing of cytological specimens. The image capture apparatus 100 employs a camera to capture digital images of a slide 102. Image capture of a specimen 103 on the slide 102 is performed by subdividing the slide 102 into a plurality of equally sized regions, designated by the dotted lines in the slide 102, and individually capturing a digital image of a region. The digital image of the region is stored in a memory once captured and is analyzed by mapper 104 which operates to analyze the region for the presence of cytological material. If any cytological material is detected, the region is designated by the mapper as a screenable region. Once the region is analyzed, a digital image of another region of the slide is captured at 100 and analyzed at 104. This sequence is repeated until each region of slide 102 has been captured and analyzed.

Once all regions of the slide 102 have been captured and analyzed (106), the mapper 104 generates, as seen at 107, a plurality of tiles, which are shown as circles within the slide 102 at the screening station 110. The tiles shown in FIG. 1 are simplified for ease of illustration. Each of the tiles is preferably the same size and corresponds to a field of view selected by the cytotechnologist for the microscope at the screening station. Collectively, the tiles surround all of the cytological material determined by the mapper to be required for viewing by the cytotechnologist. Once the tiles are generated, the mapper, as seen at 108, employs a routing function to generate a plurality of viewing coordinates which determine the sequence in which the tiles may be viewed by a cytotechnologist at screening station 110. The coordinates are then transmitted upon request by a screening station 110 to that screening station (described in further detail below) which preferably takes the form of a microscope employing a motorized stage to move the slide 102 beneath a lens of the microscope in accordance with the sequence of coordinates received from the mapper.

The sequence in which the tiles are viewed is advantageously selected by the mapper to reduce the amount of time required for the screening station 110 to move between the tiles and to maximize the practical degree of scene continuity. Thus, the mapper 104 reduces the average time required for the cytotechnologist to screen the specimen contained on slide 102 in two ways. First, the regions of the slide which do not contain any cytological material are eliminated by the mapper, thus eliminating the need for the cytotechnologist to visually perform such a task. Second, the path between the regions which contain cytological material is optimized, thus reducing the amount of time required for the motorized stage employed by the microscope of the station 110 to move from one region to the next.

The regions of the slide shown in FIG. 1 are simplified for sake of illustration. In practice, a slide will typically have far more regions than shown in FIG. 1. For example, a typical slide which measures approximately 75 mm×25 mm, with an area of roughly 50 mm×25 mm being occupied by a specimen. Such a slide will contain regions of approximately 2.5 mm×2.5 mm, totaling approximately 200 regions for the slide.

The image capture apparatus 100 preferably takes the form of a CCD (Charge Coupled Device) type scientific grade type camera with a 1K×1K or larger format, and a class 3 or better sensor. Such a camera is available commercially under the trade name ES-1 from Kodak Corporation, Rochester, N.Y., and is also available from Pulnix America, Sunnyvale, Calif. Such a camera preferably is characterized by an active sensor area of 9 mm×9 mm or larger and with a pixel spacing of nine (9) microns or finer and can capture images at a rate of at least 30 frames/second, and provide a digital output at a minimum rate of 30 Mhz. The optical system is configured to provide an effective pixel resolution of approximately 2.4 microns at the sample. While such a resolution is appropriate for the preferred embodiment described herein, it may be changed for other applications. The specifications stated herein are illustrative of a particular preferred embodiment and may be altered. For instance, a camera with a format larger than 1K×1K would reduce the number of images to be captured because each captured image would contain a larger portion of the slide. A pixel spacing of finer than 9 microns would result in higher resolution.

The camera provides its digital output to a frame grabber which operates to store the digital data received from the camera. The frame grabber preferably employs a PCI type interface and is characterized by a data transfer rate of at least 50 Mhz. Preferably the frame grabber also employs digital signal processing for shading correction and blob finding. A preferred frame grabber takes the form of a Data Raptor type frame grabber available from Bit Flow Corp., Woburn, Mass. In an alternative embodiment, the frame grabber may perform certain image enhancement functions by way of specialized hardware devices to provide a speed increase over performing such functions in software. For instance, the frame grabber may be configured with specialized hardware such as digital signal processing circuitry to perform histogram calculations performed in the preferred embodiment described herein in software.

The screening station 110 preferably takes the form of a microscope employing a motorized stage and motorized focusing which may be controlled by the operator of the station by way of an ergonomic input device which allows simple and rapid control of the stage and focusing. The screening station may also be operated under computer control or under combined manual and computer control. The screening station is coupled to the mapper 104 via a serial link and receives from the frame grabber positional information in the form of coordinates of regions to be viewed by the station operator. A preferred screening station is available from AccuMed International, Chicago, Ill., under the trade name AcCell™ Series 2000.

In a preferred embodiment, the mapper and image capture apparatus are contained in a single housing and the mapper is coupled to the screening station by way of a local area network. While neither the physical structure of the mapper and image capture apparatus or the manner of coupling the mapper to the screening station is critical, such an arrangement allows the mapper and image capture apparatus to be physically separate from the screening station and allows the mapper to transmit and receive information with a plurality of screening stations. Alternative arrangements of the manner in which the mapper and screening station are coupled, such as by way of example, a direct serial link, will be apparent to those skilled in the art in view of the present disclosure.

An operator wishing to use the screening station 110 to view a slide inserts the slide or a plurality of slides into a slide carrier which is then inserted into a magazine contained on the screening station. The system extracts a slide from the magazine and scans, using a bar code reader, a bar code, which is affixed to each slide. The identity of the slide, as determined by the scanned bar code is used by the system to retrieve coordinates from the mapper 104. The slide is then transported from the magazine onto the stage which is then positioned in accordance with a first set of coordinates received from the mapper 104. The operator may then view the slide and by use of the above mentioned ergonomic input device control the focus as well as the speed of the stage. If desired the operator can stop movement of the stage and then restart the movement. Moreover, the operator may enter a manual mode where control over viewing of the slide is fully manual and any portion of the slide may be viewed in the sequence desired by the operator. Additional aspects of the operation of the screening station are described in the following U.S. Patent Applications, which are each assigned to the assignee of the present application, and which are hereby incorporated by reference:

"System for Simplifying the Implementation of Specified Functions", Ser. No. 08/529,188.

"Automated Specimen Handling System and Method for Sorting the Specimens", Ser. No. 08/528,789.

"Specimen Management System", Ser. No. 08/528,793.

Figure 2:
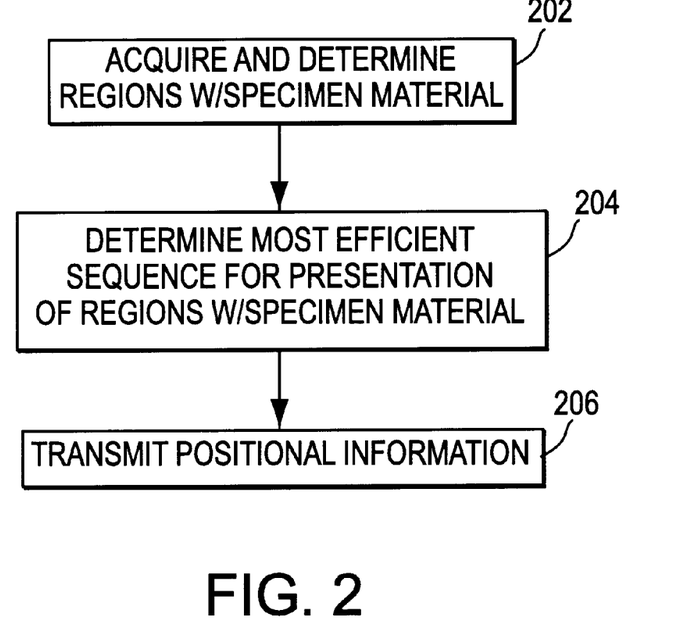
FIG. 2 is a flow diagram illustrating operation of a preferred embodiment.

The functions performed by the mapper 104 are illustrated in flow chart form in FIG. 2. Preferably the mapper is implemented as a software program stored in a semiconductor, magnetic of other similar type of storage device and executed by a general purpose digital computer. As seen at 202, the mapper acquires an image of each region of the slide from the image capture block 100 of FIG. 1, and determines which regions contain cytological material. New region boundaries are then determined in such a manner as to include all detected material within the regions while, to the greatest extent practical, excluding those portions of the slide not containing material to be presented from the regions. Next, at 204, the most efficient sequence for presentation of the regions containing cytological material to the cytotechnologist is determined. Finally, at 206, positional information in the form of a sequence of coordinates is transmitted to the screening station 110.

Figure 3:
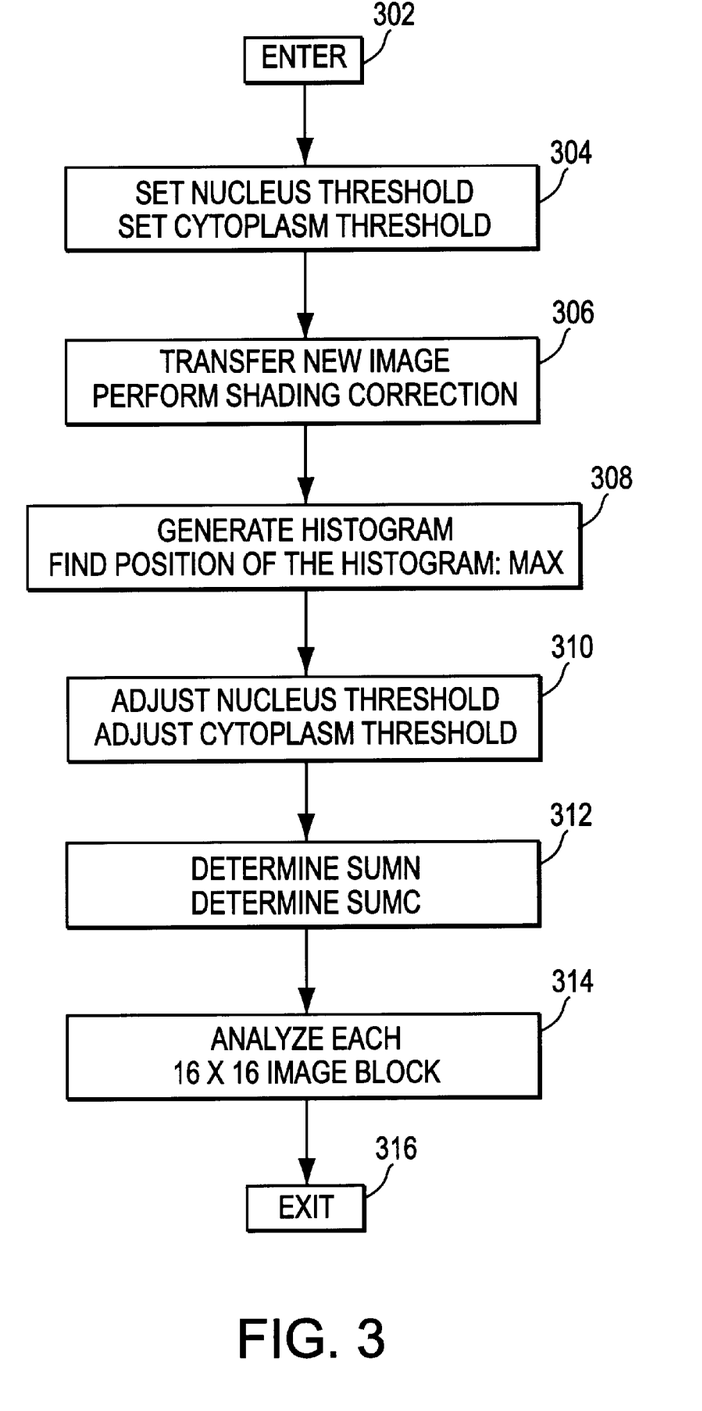
FIG. 3 is a flow diagram illustrating a portion of FIG. 2 in greater detail.
Figure 4A:
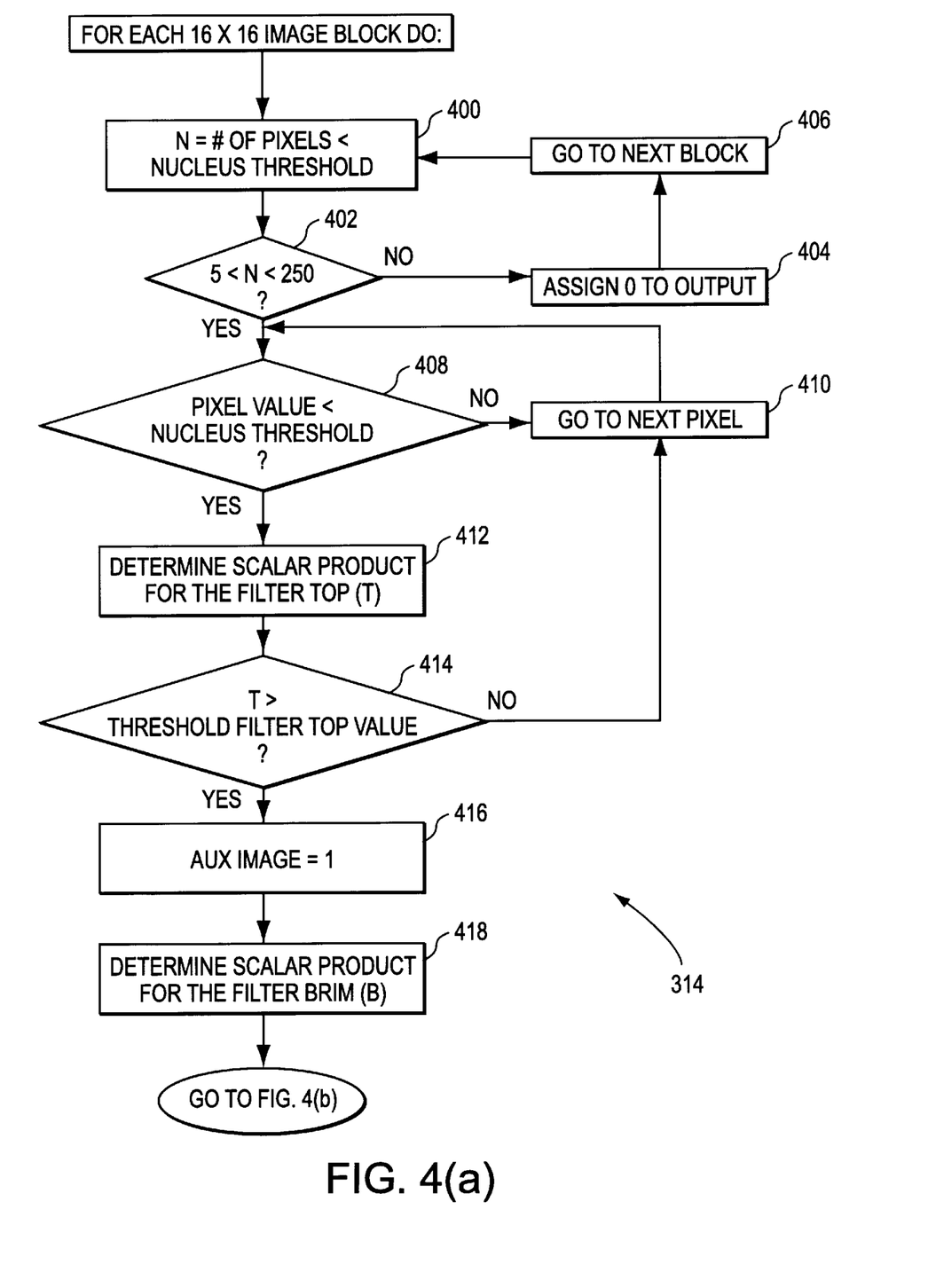
FIGS. 4(a) and 4(b) are flow diagrams illustrating a portion of FIG. 3 in greater detail.
Figure 4B:
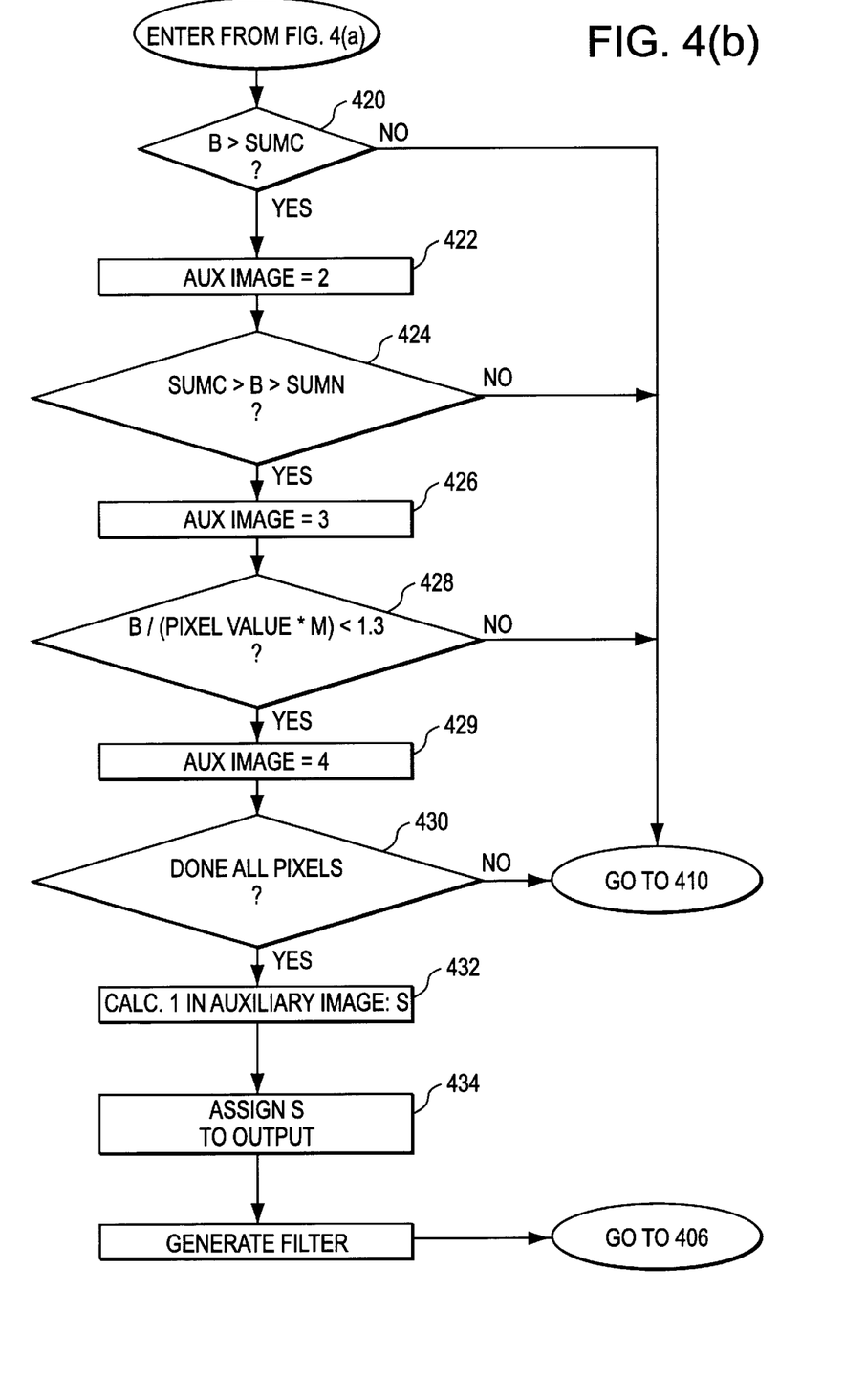

As illustrated in FIG. 1, mapper 104 analyzes each region of the slide 102 by first subdividing each region into a plurality of equally sized blocks, designated by dotted lines within region 112, and then individually analyzing each picture element (pixel), designated by dotted lines within block 114, within each block. Preferably, the number of regions is large enough so that any one region occupies no more than one-quarter of the area of the 100% coverage field of view of a 10× screening objective used in the screening station 110. Each region preferably is divided into a 64×64 matrix of blocks, with each block containing a matrix of 16×16 pixels. The camera/objective combination of the image capture apparatus 102 is advantageously chosen to provide a nominal resolution of 2.5 microns at the specimen, thus ensuring the detection of all objects larger than 5 microns in diameter. Preferably, the mapper is implemented as a stored program executed by a general purpose computer. FIGS. 3, 4(a) and 4(b) illustrate the operation of the mapper in further detail.

The mapper program is entered at step 302 and at step 304, a nucleus and a cytoplasm threshold are obtained from values stored in memory accessible to the mapper. Each threshold establishes an initial gray scale intensity level used to compare against the gray scale intensity of the pixels being analyzed. Preferably a gray scale represented by eight bits (one byte) is used to provide a range of 256 gray scale values from zero (0) to two-hundred fifty-five (255). In such a range a value of zero indicates a pixel which is completely black, and a value of 255 indicates a pixel which is white, or clear. Preferably, the nucleus threshold is set on such a gray scale to an initial value of 150 and the cytoplasm threshold is set to an initial value of 200. In one embodiment, as described above, the initial values of the nucleus and cytoplasm thresholds are set empirically and then adjusted based upon the image data. In another embodiment, the initial values are determined adaptively from the image histogram. The empirical approach tends to be more computationally simple and efficient if the image has been shading corrected and scaled. The adaptive approach gives better performance if the image has been shading corrected but not scaled. A pixel exhibiting a gray scale intensity below the nucleus threshold may be representative of nuclear material and a pixel exhibiting a gray scale intensity above the nucleus threshold and below the cytoplasm threshold may be representative of cytoplasmic material. A pixel exhibiting a gray scale intensity above the cytoplasm threshold is determined by the mapper to be neither nuclear nor cytoplasmic material.

At 306, the image of the region in question obtained by the frame grabber is transferred to the mapper and shading correction of the image is performed to correct for non-uniformities in illumination of the image which may occur due to a variety of factors including defects or shortcomings in the camera. Shading correction is performed by generating, prior to initiation of the mapper routine, a pixel correction map which contains a correction value corresponding to each pixel in the frame grabber. The pixel correction map is generated by taking an image with the frame grabber of a clean, blank slide. The resulting image, the pixels of which are expected to each have a gray scale value of 255, is then analyzed and the pixel map is generated so that each pixel has a corresponding correction value which, when added to the value of the pixel in the image of the blank slide, results in a gray scale value of 255. Performing the shading correction step seen at 306 requires the addition of each pixel correction value to the corresponding pixel.

At steps 308 and 310, the initial nucleus and cytoplasm thresholds are adjusted to correct for any background material, such as mucus, on the specimen which may affect the analysis of the pixels. The adjustment is preferably done by calculating a histogram of the gray scale values of the pixels in the region in question. The gray scale value having the highest occurrence in the histogram is designated at step 308 as the variable MAX, and at step 310, the nucleus and cytoplasm thresholds are adjusted in accordance with the following relationships:

Nucleus Threshold=(Nucleus Threshold+MAX)−255 (1)

Cytoplasm Threshold=(Cytoplasm Threshold+MAX)−255 (2)

In equations (1) and (2) above, the value 255 is the maximum value (white) in the utilized gray scale.

At step 312, a nucleus pixel threshold (SUMN) and a cytoplasm pixel threshold (SUMC) are calculated in accordance with the following relationships:

SUMN=L*Nucleus Threshold (3)

SUMC=M*Cytoplasm Threshold (4)

Figure 5:
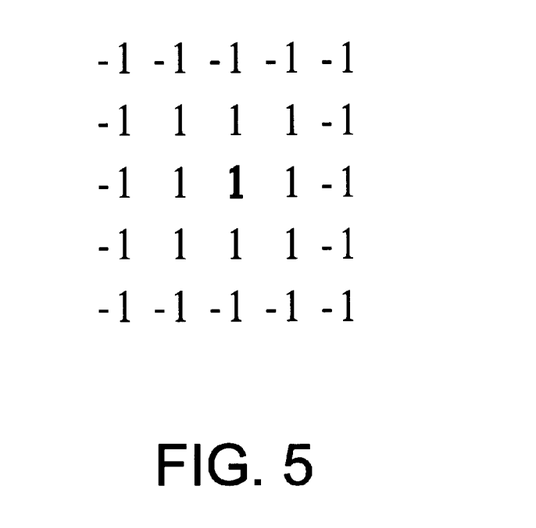
FIG. 5 is an illustration of a preferred filter employed by a preferred embodiment.

In equations (3) and (4) above, the values L and M are representative of a filter which is preferably employed to analyze individual pixels as a function of surrounding pixels. FIG. 5 of the drawings shows a preferred form of the filter employed to perform such a function. Shown in FIG. 5 is a matrix of twenty-five pixels, with the pixel in question shown at the center of the matrix, and designated by the numeral "1". The eight pixels immediately surrounding the pixel in question, are also designated by the numeral "1" and, like the pixel in question, represent pixels with gray scale intensities which are below the nucleus threshold, and thus represent nuclear material. The sixteen pixels at the periphery of the matrix, which are designated by the numeral "-1" represent pixels with gray scale intensities which are between the nucleus and cytoplasm thresholds and thus represent cytoplasmic material. Thus the filter shown in FIG. 5, referred to herein as a "tophat filter" determines a pixel to represent nuclear material if the pixel in question has a gray scale intensity less than the nucleus threshold, and if the eight immediately surrounding pixels also have a gray scale intensity less than the nuclear threshold, and if the sixteen pixels immediately surrounding the aforesaid eight pixels have a gray scale intensity between the nucleus and the cytoplasm thresholds.

The value L as used in equation (3) above is indicative of the number of pixels in the tophat filter representing nuclear material which surround the pixel in question. Thus, in the tophat filter of FIG. 5, L equals the value eight (8). The value M as used in equation (4) above is indicative of the number of pixels in the tophat filter representing cytoplasmic material, which in the tophat filter of FIG. 5 equals the value sixteen. Once the values SUMN and SUMC are determined, each block of the region in question is individually analyzed as seen at 314 in a manner more fully shown in FIGS. 4(a) and 4(b).

At 400, the number of pixels in the block exhibiting a gray scale intensity less than the nucleus threshold (N) is determined, and at step 402, the value N is compared to an empirically predetermined range which by way of example has a value five as a minimum and a value 250 as a maximum. The comparison at step 402 advantageously provides a rapid and initial determination of whether the block in question requires further analysis to determine the presence of viewable specimen material. If the number of pixels in the block which are less than the nucleus threshold is less than five, then the block is determined to be free of cellular material, and if the number of pixels in the block which are less than the nucleus threshold is greater than 250 then the block is determined to contain material other than isolated cellular material. In either of these situations, no further analysis of the pixels in the block is performed, and the block is not included among the blocks to be viewed by an operator at the screening station 110. At 404, a value of zero is assigned to the block and analysis of the next block is performed. The lower value (5) of the range is advantageously selected to eliminate from further analysis blocks which may have some pixels, caused by dust or other types of non-cellular material, which are below the nucleus threshold, but which are free of cellular material. The upper value (250) of the range is advantageously selected to eliminate from further analysis, blocks which contain material other than cellular material, such as labels on the slide, which allow such little transmission of light through the slide to prevent further analysis of the material.

If N is within the range established at step 402, then starting at step 408, each pixel of the block in question is individually analyzed and categorized as being in one of four categories. If the pixel in question meets the criteria at 414, then the pixel is initially determined to be in category 1 and additional analysis is performed at steps 420, 424 and 428 to determine if that pixel should be moved to category 2, 3 or 4. Pixels eventually determined to be in category 1 are those pixels which are deemed to be representative of nuclear material. Pixels eventually determined to be in category 2 are those pixels which are deemed to be representative of superficial squamous cells. Pixels eventually determined to be in category 3 are those pixels which are deemed to be representative of cytoplasmic overlap in the specimen. Pixels eventually determined to be in category 4 are those pixels which are deemed to be representative of an artifact, such as dust, bubbles and scratches as well as biological material that is not of interest. For example, some specimens include cell fragments as well as intact cells. The former are generally not of interest. Similarly, some labs are not interested in bacteria, yeasts, fungi and similar objects present in specimens that are being screened for the presence of cancer. The distinctions between categories 2, 3 and 4 are of use only during testing of the routine and are not used in determining whether the block in question contains viewable cellular material, i.e. cellular material required to be viewed by the cytotechnologist. If any pixels in the block in question are determined to be in category 1, then the block is included as one of the blocks presented in the routing path to the cytotechnologist for viewing at the screening station 110.

At step 408, the gray scale value of the pixel in question is compared to the nucleus threshold, and if the gray scale value is not less than the nucleus threshold, then the routine proceeds to analyze the next pixel. Otherwise, at step 412 a scalar product for the filter top (T) is generated by adding the gray scale intensity of the pixel in question with the surrounding eight pixels. The value T is compared at step 414 to a threshold filter top value, and if T is not greater than the threshold filter top value then the routine proceeds to the next pixel. The threshold filter top value is preferably generated in accordance with the following relationship:

Threshold Filter Top Value=Pixel Gray Scale Value*M*1.075 (5)

where, 1.075 is a predetermined scaling factor. If at 414, T is greater than the threshold filter top value, then at 416 the block in question is assigned a value of one, and at 418, a filter brim value (B) is generated by adding the intensity of the pixel in question with the 16 pixels at the periphery of the filter. The routine continues in FIG. 4(b), where at 420, the filter brim value (B) is compared to the cytoplasm pixel threshold (SUMC), and if B is not greater SUMC then the routine proceeds to the next pixel. Otherwise, at step 422, the pixel in question is assigned to category 2, and at step 424, B is checked to determine if it is within a range established by SUMC and SUMN. If B is outside of such range, then the routine proceeds to the next pixel. Otherwise, at step 426, the pixel in question is assigned to category 3 and at step 428, the routine determines if the level of contrast between the top and brim values are less than a predetermined threshold value, selected to be a value of 1.3, and if not then the routine proceeds to the next pixel. Otherwise, the pixel in question is assigned to category 4. Once all pixels are analyzed, the number of pixels in category I is determined at 432.

At step 434 a scanning speed is determined for the block in question. The mapper advantageously determines a scanning speed, the speed at which the microscope stage will move the slide under the lens for the block in question, as a function of the number of pixels containing viewable cellular material, in other words, the number of pixels in category 1. This advantageous feature causes blocks which have been determined to contain little viewable cellular material to be scanned faster than blocks determined to contain more viewable cellular material.

The scanning speed is determined as a function of the amount of time required of a cytotechnologist to visually scan a field of view and to have confidence that all objects in the field of view were noticed. The scanning speed is determined as a function of such a range and the number of pixels determined to represent viewable cellular material, as well as the distribution of the pixels within the tile. Thus, regions containing more cytological material will be scanned slower than regions containing less cytological material, thus allowing the cytotechnologist more time for analysis of a region which contains a large amount of cytological material. The number of pixels in each block is represented by the count S as determined at step 432. Equation (6) below shows the manner in which a measure of image complexity is calculated:

$$C = \sum_{i=0}^{N-1} S_i d_i \qquad (6)$$

where, N is the number of map pixels in the tile;

$S_i$ is the map pixel value; and $d_i$ is the distance from the pixel to the center of the tile. The equation above advantageously generates a scanning speed a measure of image complexity that can be used to derive a which is related to the number of pixels containing viewable cellular material but yet which is within a pre-defined range to ensure adequate viewing time. The viewing time also has a maximum limit to prevent overly long viewing times.

Figure 6A:
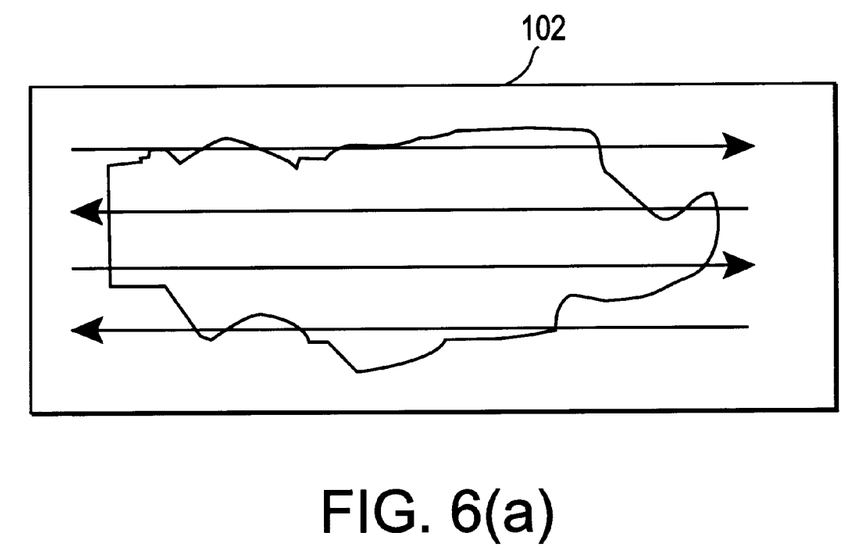
FIGS. 6(a) and 6(b) are simplified illustrations showing primary viewing patterns generated by a preferred embodiment.
Figure 6B:
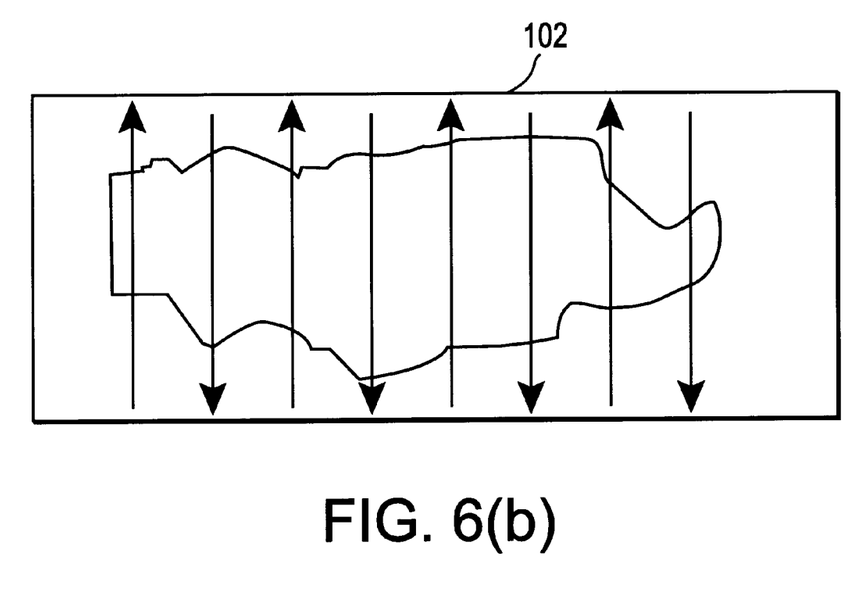

Once all regions of the slide have been analyzed as described above to determine the presence and location of the cytological material on the slide, the mapper at step 435 generates tiles, which each represent a field of view for the screening station, for viewing of the cytological material by a cytotechnologist. Preferably, four sets of tiles are generated, with two sets being generated for viewing of the tiles in a primary vertical pattern and two sets being generated for viewing of the tiles in a primary horizontal pattern. Of the two sets of tiles generated for primary vertical viewing, one set corresponds to the field of view created by a 10× magnification at the screening station, and a second set corresponds to the field of view created by a 20× magnification at the screening station. A 10× magnification corresponds to a circular field of view of approximately 2.2 mm in diameter and a 20× magnification corresponds to a circular field of view of approximately 1.1 mm in diameter. Each circular tile is preferably smaller than the field of view for a selected magnification. By way of example, a circular tile may be 200 microns smaller than the field of view for a selected magnification. Alternatively, each of the tiles may take the form of square with sides, by way of example, of approximately 1.56 mm. While either circular or square shaped tiles may be used to advantage, circular shaped tiles have been found to require a fewer number of tiles than square shaped tiles to cover the viewable material on a slide, thereby reducing the fields of view presented to the cytotechnologist. Similar sets are created for primary horizontal viewing. Thus, the cytotechnologist may select one of two magnifications for viewing of the tiles in either a primary horizontal or primary vertical viewing pattern. FIG. 6(*a*) of the drawings shows an example of a primary horizontal viewing pattern and FIG. 6(*b*) of the drawings shows an example of a primary vertical viewing pattern. While the fields of view presented to the cytotechnologist will deviate from a horizontal or vertical pattern, the overall path taken to present the tiles to the operator in a primary horizontal pattern will resemble a serpentine path moving horizontally from one end of the slide to the other. Similarly, the primary vertical pattern will resemble a serpentine path moving vertically from one end of the slide to the other with slight deviations.

Figure 7:
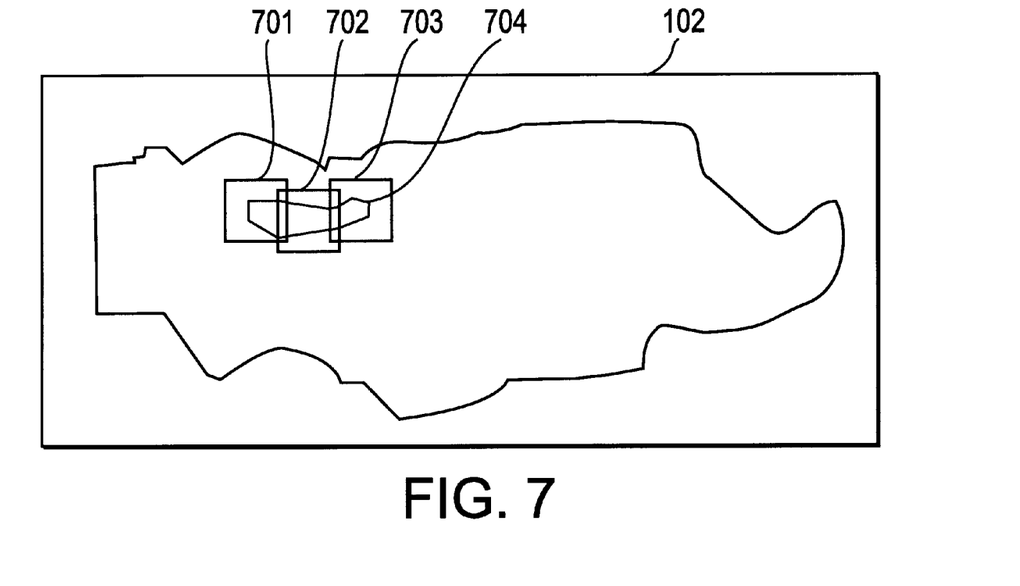
FIG. 7 is a simplified illustration showing a manner in which tiles may be generated by a preferred embodiment.
Figure 8:
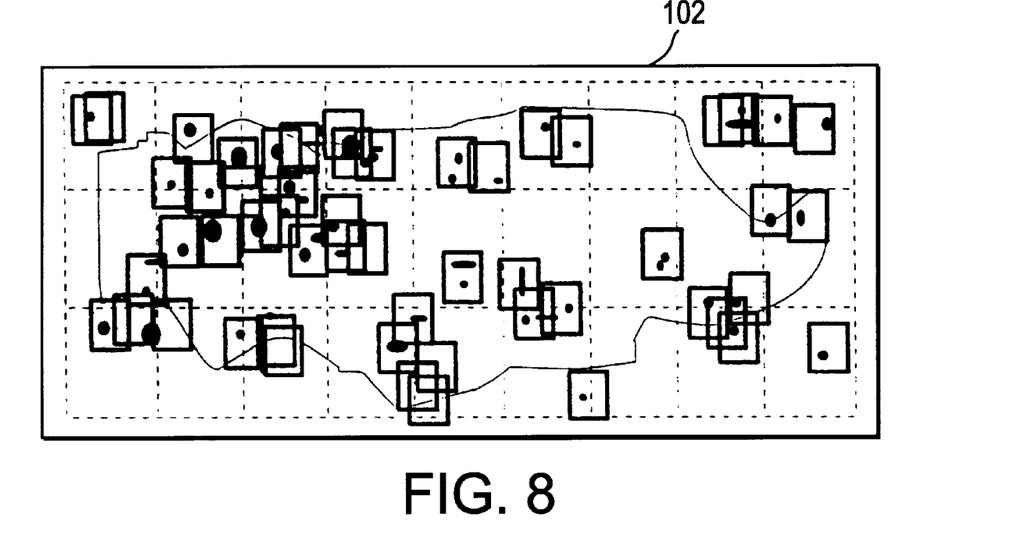
FIG. 8 is an illustration showing an alternative embodiment of the views seen in slide 102 in FIG. 1.

The generation of tiles is preferably performed in a manner to cover all of the identified viewable material with a minimum number of tiles and a minimum distance required to move between the tiles. Preferably, tiles are positioned so that the viewable material is positioned at the center of the tile. As seen in FIG. 1, tiles may be separate to cover viewable material which can be covered by a single tile. Tiles may also overlap one another (as seen in FIG. 1) to cover viewable material which requires multiple tiles to cover the material. Advantageously, overlapping tiles may reduce the distance from tile to tile required to present certain material to a cytotechnologist. For instance, as shown in FIG. 7, tiles 701, 702 and 703 are generated in a primary horizontal fashion so as to overlap one another to cover the material seen at 704. Advantageously, the field of view merely needs to be shifted from left to right slightly to present three fields of view to view the material 704 in its entirety. Moreover, the overlap provides continuity to the field of view to further simplify the analysis by the cytotechnologist. A focal position for each tile is also generated in a manner which preferably maximizes contrast and spatial frequency content in the image.

Preferably, the four sets of tiles are stored in a text type file and the coordinates transmitted by the mapper to the screening station includes four values. Two values define a starting position in the region to be viewed, one value defines a focal position for focusing of the microscope lens in the region to be viewed, and one value is a scanning speed value which determines how fast the stage is moved under the lens for the region to be viewed.

To view a slide, a cytotechnologist loads a cassette with one or more slides which has been analyzed by the mapper, selects a magnification and informs the screening station by entry of appropriate commands through a control panel on the screening station of the desired viewing pattern (horizontal or vertical). The cassette is inserted appropriately into the screening station which selects a slide and reads an identification code on the slide in the form of a bar code. The screening station determines the field of view corresponding to the selected magnification, and then searches an electronic directory for the presence of the identification code on the slide, and if the directory contains the identification code, then the screening station uses the information from the directory to retrieve a text file containing the set of tiles corresponding to the magnification and desired viewing pattern selected by the cytotechnologist.

In an alternative embodiment, the mapper can analyze each region of the slide in a manner shown in the steps of the drawings through step 434. Then, upon a request from the screening station for tiles corresponding to a particular selected magnification and viewing pattern the mapper could generate the appropriate tiles and routing pattern corresponding to the selected magnification and viewing pattern. Such a technique may result in a slight delay while the mapper generated the tiles and routing map, but would reduce the amount of storage required to store the files containing the four sets of tiles corresponding to two magnifications and two viewing patterns.

It is to be understood that the specific mechanisms and techniques which have been described are merely illustrative of one application of the principles of the invention. Numerous modifications may be made to the methods and apparatus described without departing from the true spirit and scope of the invention.

The claims should not be read as limited to the described order of elements unless stated to that effect. In addition, use of the term "means" in any claim is intended to invoke 35 U.S.C. § 112, paragraph 6, and any claim without the word "means" is not so intended.

What is claimed is:

1. A method of assisting a human observer to screen a cytological specimen, said method comprising, in combination:

acquiring into a machine a set of digital image data representing said specimen;

said machine analyzing said digital image data and thereby identifying regions in said specimen containing diagnostically significant material, each of the regions that said machine determines to contain diagnostically significant material defining a screenable region, whereby, said machine may exclude from further analysis any region that said machine determines to not contain diagnostically significant cytological material;

said machine generating a function defining, individually with respect to each screenable region, a speed for presentation of said screenable region to said human observer, wherein said speed for presentation of a screenable region to said human observer defines a scanning speed for movement of said cytological specimen in relation to a microscope lens for displaying said region via a microscope to said human observer, and wherein said speed is slower for a screenable region that contains a greater quantity of diagnostically significant cytological material than another screenable region and said speed is faster for a screenable region that contains a lesser quantity of diagnostically significant cytological material than another screenable region; and said machine employing said function to control presentation of said screenable regions to said human observer, whereby said function may give a human observer more time to view a screenable region containing a greater quantity of diagnostically significant cytological material, and vice versa.

2. A method as claimed in claim 1, wherein said speed is slower for a screenable region that contains more widely distributed diagnostically significant material than another screenable region, and said speed is faster for a screenable region that contains less widely distributed diagnostically significant material than another screenable region, whereby said function may give a human observer more time to view a screenable region containing more widely distributed diagnostically significant material.

3. A method as claimed in claim 1, wherein said digital image data represents pixels cooperatively defining an image of said specimen, and wherein said machine identifying regions in said specimen containing diagnostically significant material comprises said machine analyzing an intensity of each of the pixels cooperatively defining a region of said specimen and determining, with respect to said pixel, whether said intensity may represent diagnostically significant material.

4. A method as claimed in claim 1, wherein said specimen comprises a cytological specimen, wherein diagnostically significant material comprises cytological material, and wherein said machine determining whether said intensity may represent diagnostically significant material comprises said machine comparing said intensity to a nuclear threshold intensity and a cytoplasm threshold intensity.

5. A method as claimed in claim 1, further comprising said machine maintaining in a data storage medium a set of coordinates corresponding to locations of screenable regions in said specimen, wherein said presentation function further defines a sequence for presentation of said screenable regions to said human observer, said sequence being keyed to said stored coordinates corresponding to respective screenable regions.

6. A method as claimed in claim 5, wherein said coordinates include a focal position respectively for each screenable region and said presentation function keyed to said stored coordinates thereby defines focal position for presentation respectively of each screenable region via a microscope.

7. A method as claimed in claim 5, wherein said stored coordinates are generated as a function of at least a first magnification selectable for presentation of said specimen via a microscope.

8. A method as claimed in claim 5, wherein presentation of screenable regions to a human observer comprises moving said specimen in relation to a microscope lens so as to display said screenable regions for viewing by said human observer via said microscope.

9. A method as claimed in claim 8, wherein said machine configures said sequence so as to minimize physical movement of said specimen in relation to said microscope lens.

10. A method as claimed in claim 9, wherein said machine configures said sequence for presentation of said screenable regions in a serpentine path.

11. A method of assisting an observer to analyze a cytological specimen via a microscope screening station, said microscope screening station comprising a microscope with a lens and a motorized stage for moving said specimen across said lens, said method comprising, in combination:

receiving into a machine a set of digital data representing an image of said specimen, said image being comprised of pixels;

said machine analyzing said digital data and thereby identifying cytological material in said specimen;

said machine maintaining in a data storage medium a set of spatial coordinates associated with each of a plurality of regions of said specimen that collectively contain the cytological material that said machine identifies in said specimen, wherein said machine identifies a quantity of cytological material respectively in each of said regions;

said machine generating a routing path keyed to said coordinates, wherein (i) said routing path defines a sequence for presentation of said regions to a human observer via said microscope, (ii) said sequence is arranged to minimize movement of said specimen across said lens, (iii) said routing path defines for each of said regions a speed for movement of said specimen across said lens, and (iv) said speed for each given region is a function of at least the quantity of cytological material that said machine identifies respectively in said given region; and said machine applying said routing path to control movement of said motorized stage so as to present said regions to said human observer via said microscope according to said sequence and speeds, whereby said speed will be slower for regions containing more cytological material than other regions, thereby allowing said human observer more time for analysis of said regions containing more cytological material, and vice versa.

12. A method as claimed in claim 11, wherein said spatial coordinates include focal positions for said regions.

13. A method as claimed in claim 11, wherein said machine analyzing said data and thereby identifying cytological material in said specimen comprises said machine individually analyzing each pixel represented by said digital data to determine if said pixel represents cytological material.

14. A method as claimed in claim 13, wherein individually analyzing each pixel represented by said digital data to determine if said pixel represents cytological material comprises comparing a gray scale value of said pixel to a nucleus threshold value and to a cytoplasm threshold value.

15. A method as claimed in claim 11, further comprising said machine identifying areas of said specimen that do not contain cytological material, and said machine excluding such areas from presentation as defined by said routing path.

16. A method as claimed in claim 11, wherein said spatial coordinates are generated as a function of at least a first magnification selectable for presentation of said specimen via said microscope.

17. A method as claimed in claim 11, wherein said machine configures said sequence for presentation of said regions in a serpentine path.

18. A general purpose computer programmed with a set of machine language instructions for carrying out the following functions so as to assist a human observer in analyzing a specimen:

receiving a set of digital image data representing said specimen;

analyzing said digital image data and thereby identifying regions in said specimen containing diagnostically significant material, each of the regions determined to contain diagnostically significant material defining a screenable region;

generating a function defining, individually with respect to each screenable region, a speed for presentation of said screenable region to said human observer, wherein said speed is slower for a screenable region that contains more diagnostically significant material than another screenable region and said speed is faster for a screenable region that contains less diagnostically significant material than another screenable region; and employing said function to control presentation of said screenable regions to said human observer, whereby said function may give a human observer more time to view a screenable region containing more diagnostically significant material.

19. A computer programmed with a set of machine language instructions for carrying out a set of functions so as to assist an observer to analyze a cytological specimen via a microscope screening station, wherein said microscope screening station comprises a microscope with a lens and a motorized stage for moving said specimen across said lens, and said set of functions comprises, in combination:

receiving a set of digital data representing an image of said specimen, said image being comprised of pixels;

analyzing said digital data and thereby identifying cytological material in said specimen;

maintaining in a data storage medium a set of spatial coordinates indicative of each of a plurality of regions of said specimen that collectively contain the cytological material that said computer identifies in said specimen, wherein said computer identifies a quantity of cytological material respectively in each of said regions; and generating a routing path keyed to said coordinates, wherein (i) said routing path defines a sequence for presentation of said regions to a human observer via said microscope, (ii) said sequence is arranged to minimize movement of said specimen across said lens, (iii) said routing path defines for each of said regions a speed for movement of said specimen across said lens, and (iv) said speed for each given region is a function of at least the quantity of cytological material that said computer identifies respectively in said given region, whereby, said routing path may be applied to control movement of said motorized stage so as to present said regions to said human observer via said microscope according to said sequence and speeds, and whereby said speed will be slower for regions containing more cytological material than other regions, thereby allowing said human observer more time for analysis of said regions containing more cytological material, and vice versa.

20. A cytological specimen analyzer comprising:

a camera which generates digital data indicative of an image captured by said camera;

a storage apparatus coupled to said camera which stores said digital data;

an image analyzer which analyzes said digital data and thereby learns information about diagnostically significant material contained respectively in particular regions of the cytological specimen and which stores coordinates indicative of particular regions of said cytological specimen;

a router which generates a routing function keyed to said stored coordinates, said routing function defining a sequence for presentation of microscope fields of view corresponding to images of particular regions of said cytological specimen and defining, respectively for each given region to be presented, a speed for presentation of said given region, said speed being based at least in part on information that said image analyzer learns about diagnostically significant material contained respectively in said given region; and a screening station which employs a microscope with a motorized stage which responds to coordinates received from said router and which presents said sequence of microscope fields of view according to said speeds defined by said routing function.

21. A specimen analyzer as claimed in claim 20, wherein said speed for presentation of a given region of said specimen is based at least in part on a measure of quantity of diagnostically significant material contained in said given region as determined by said image analyzer.

22. A specimen analyzer as claimed in claim 20 wherein said speed for presentation of a given region of said specimen is based at least in part on a measure of spatial distribution of diagnostically significant material contained in said given region as determined by said image analyzer.

23. A specimen analyzer as claimed in claim 20, wherein said diagnostically significant material nuclear material.

24. A specimen analyzer as set forth in claim 20 further comprising a plurality of screening stations, which each employ a microscope with a motorized stage, each of said screening stations comprising:

means for transmitting specimen identification information to said router; and means, responsive to coordinates corresponding to said specimen identification information received from said router, for causing said motorized stage to respond to said received coordinates to present said sequence of fields of view according to said speeds defined by said routing function.

25. A method of assisting an observer to analyze a cytological specimen via a microscope screening station, said microscope screening station comprising a microscope with a lens and a motorized stage for moving said specimen across said lens, said method comprising, in combination:

receiving into a machine a set of digital data representing an image of said specimen, said image being comprised of pixels;

said machine analyzing said digital data and thereby identifying cytological material in said specimen;

said machine maintaining in a data storage medium a set of spatial coordinates associated with each of a plurality of regions of said specimen that collectively contain the cytological material that said machine identifies in said specimen;

said machine generating a routing path keyed to said coordinates, wherein (i) said routing path defines a sequence for presentation of said regions to a human observer via said microscope, (ii) said sequence is arranged to minimize movement of said specimen across said lens, (iii) said routing path defines for each of said regions a speed for movement of said specimen across said lens, and (iv) said speed for each given region is a function of at least a distribution of cytological material that said machine identifies respectively in said given region; and said machine applying said routing path to control movement of said motorized stage so as to present said regions to said human observer via said microscope according to said sequence and speeds, whereby said speed may be slower for regions containing more widely distributed cytological material than other regions, thereby allowing said human observer more time for analysis of said regions containing more widely distributed cytological material, and vice versa.

26. A computer programmed with a set of machine language instructions for carrying out a set of functions so as to assist an observer to analyze a cytological specimen via a microscope screening station, wherein said microscope screening station comprises a microscope with a lens and a motorized stage for moving said specimen across said lens, and said set of functions comprises, in combination:

receiving a set of digital data representing an image of said specimen, said image being comprised of pixels;

analyzing said digital data and thereby identifying cytological material in said specimen;

maintaining in a data storage medium a set of spatial coordinates indicative of each of a plurality of regions of said specimen that collectively contain the cytological material that said computer identifies in said specimen; and generating a routing path keyed to said coordinates, wherein (i) said routing path defines a sequence for presentation of said regions to a human observer via said microscope, (ii) said sequence is arranged to minimize movement of said specimen across said lens, (iii) said routing path defines for each of said regions a speed for movement of said specimen across said lens, and (iv) said speed for each given region is a function of at least a distribution of cytological material that said computer identifies respectively in said given region, whereby, said routing path may be applied to control movement of said motorized stage so as to present said regions to said human observer via said microscope according to said sequence and speeds, and whereby said speed will be slower for regions containing more cytological material than other regions, thereby allowing said human observer more time for analysis of said regions containing more cytological material, and vice versa.

27. A method of assisting an observer to analyze a cytological specimen via a microscope screening station, the microscope screening station comprising a microscope with a lens and a motorized stage for moving the specimen across the lens, the method comprising, in combination:

receiving into a machine a set of digital data representing an image of the specimen, the image being comprised of pixels;

the machine analyzing at least a plurality of the pixels and determining, for each such pixel, whether the pixel represents nuclear material, a pixel representing nuclear material defining a nuclear pixel;

the machine establishing a sequence of regions of the specimen for presentation to a human observer via the microscope screening station, each region of the sequence being represented by a plurality of the pixels;

the machine establishing individually for each region of the sequence a speed at which the motorized stage should move the region across the lens for presentation to the observer, the speed per region being a function of how many of the pixels representing the region are determined by the machine to be nuclear pixels, whereby the speed established for a region represented by more nuclear pixels than another region may have a slower speed than the other region; and controlling movement of the motorized stage so as to present regions of the specimen to the human observer via the microscope according to the sequence of regions and according to the scanning speed per region, whereby the speed will be slower for regions determined by the machine to contain more nuclear material, thereby allowing said human observer more time for analysis of the regions containing more nuclear material, and vice versa.

28. A computer programmed with a set of machine language instructions for carrying out a set of functions so as to assist an observer to analyze a cytological specimen via a microscope screening station, wherein said microscope screening station comprises a microscope with a lens and a motorized stage for moving said specimen across said lens, and said set of functions comprises, in combination:

receiving a set of digital data representing an image of the specimen, the image being comprised of pixels;

analyzing at least a plurality of the pixels and determining, for each such pixel, whether the pixel represents nuclear material, a pixel representing nuclear material defining a nuclear pixel;

establishing a sequence of regions of the specimen for presentation to a human observer via the microscope screening station, each region of the sequence being represented by a plurality of the pixels; and establishing individually for each region of the sequence a speed at which the motorized stage should move the region across the lens for presentation to the observer, the speed per region being a function of how many of the pixels representing the region are determined by the machine to be nuclear pixels, whereby the speed established for a region represented by more nuclear pixels than another region may have a slower speed than the other region, whereby, movement of the motorized stage may be controlled so as to present regions of the specimen to the human observer via the microscope according to the sequence of regions and according to the scanning speed per region, and whereby the speed will be slower for regions determined by the machine to contain more nuclear material, thereby allowing said human observer more time for analysis of the regions containing more nuclear material, and vice versa.

* * * * *